United States Patent
Miller

(10) Patent No.: US 9,775,963 B2
(45) Date of Patent: Oct. 3, 2017

(54) STEERABLE ENDOLUMINAL DEVICES AND METHODS

(75) Inventor: Aaron J. Miller, San Carlos, CA (US)

(73) Assignee: BioCardia, Inc., San Carlos, CA (US)

(*) Notice: Subject to any disclaimer, the term of this patent is extended or adjusted under 35 U.S.C. 154(b) by 0 days.

(21) Appl. No.: 13/288,918

(22) Filed: Nov. 3, 2011

(65) Prior Publication Data
US 2012/0123327 A1 May 17, 2012

Related U.S. Application Data

(60) Provisional application No. 61/409,929, filed on Nov. 3, 2010.

(51) Int. Cl.
*A61M 25/00* (2006.01)
*A61M 25/01* (2006.01)
(Continued)

(52) U.S. Cl.
CPC .... *A61M 25/0012* (2013.01); *A61M 25/0136* (2013.01); *A61M 25/0147* (2013.01);
(Continued)

(58) Field of Classification Search
CPC .......... A61M 25/0054; A61M 25/0012; A61M 25/0147; A61M 25/0052; A61M 25/005;
(Continued)

(56) References Cited

U.S. PATENT DOCUMENTS 5,002,041 A * 3/1991 Chikama ................ 600/139
5,125,903 A * 6/1992 McLaughlin ..... A61M 39/0606
137/849
(Continued)

FOREIGN PATENT DOCUMENTS

EP 0521595 1/1993
EP 2859907 4/2015
(Continued)

OTHER PUBLICATIONS

"along". Dictionary.com. Accessed Apr. 3, 2017. <Dictionary.comhttp://www.dictionary.com/browse/along>.*
(Continued)

*Primary Examiner* — Nathan R Price
*Assistant Examiner* — Weng Lee
(74) *Attorney, Agent, or Firm* — Crockett & Crockett, PC; K. David Crockett, Esq.

(57) ABSTRACT

A steerable endoluminal device adapted for delivery into a patient's vasculature. The device includes a tubular member having a distal deflection portion that extends to the distal end and a main body portion that extends from the deflectable portion to the proximal end, the tubular member further including a stiff portion extending along the distal deflection portion, and being formed of polymeric material, which is disposed circumferentially adjacent to the stiff portion. The stiff portion is made of a material that has an elastic modulus greater than the elastic modulus of the polymeric material. A pull wire extends between the proximal end and the distal end of the tubular member and is attached to the distal deflection portion to control deflection of the distal deflection portion of the tubular member.

18 Claims, 12 Drawing Sheets

(51) Int. Cl.
*A61M 29/00* (2006.01)
*A61M 39/06* (2006.01)
*A61M 25/06* (2006.01)

(52) U.S. Cl.
CPC ....... *A61M 25/005* (2013.01); *A61M 25/0052* (2013.01); *A61M 29/00* (2013.01); *A61M 39/06* (2013.01); *A61M 2025/0059* (2013.01); *A61M 2025/0079* (2013.01); *A61M 2025/0681* (2013.01)

(58) Field of Classification Search
CPC ...... A61M 2025/0059; A61M 25/0141; A61M 25/0144
USPC .............................. 604/523–532, 95.04, 528
See application file for complete search history.

(56) References Cited

U.S. PATENT DOCUMENTS

| | | | |
|---|---|---|---|
| 5,545,200 A * | 8/1996 | West | A61B 18/1492 606/29 |
| 6,547,787 B1 | 4/2003 | Altman et al. | |
| 6,591,472 B1 * | 7/2003 | Noone et al. | 29/417 |
| 7,048,711 B2 * | 5/2006 | Rosenman | A61M 25/0014 604/95.04 |
| 7,402,151 B2 | 7/2008 | Rosenman et al. | |
| 7,998,112 B2 * | 8/2011 | Chow et al. | 604/93.01 |
| 2001/0007933 A1 * | 7/2001 | Lesh | A61B 17/22 604/272 |
| 2001/0034514 A1 | 10/2001 | Parker | |
| 2002/0072710 A1 * | 6/2002 | Stewart | A61M 25/0082 604/164.02 |
| 2006/0135961 A1 | 6/2006 | Rosenman et al. | |
| 2006/0135981 A1 * | 6/2006 | Lenker | A61B 17/3439 606/191 |
| 2006/0264904 A1 * | 11/2006 | Kerby | A61M 25/0014 604/523 |
| 2008/0161775 A1 | 7/2008 | Potter | |
| 2008/0319420 A1 | 12/2008 | Rosenman et al. | |
| 2009/0131910 A1 | 5/2009 | Webler | |
| 2010/0049168 A1 * | 2/2010 | Parker | A61M 25/0053 604/527 |
| 2011/0112476 A1 * | 5/2011 | Kauphusman | A61M 25/0012 604/95.04 |

FOREIGN PATENT DOCUMENTS

| | | |
|---|---|---|
| JP | 03073125 | 3/1991 |
| JP | 2000000309 | 1/2000 |
| JP | 2003144554 | 5/2003 |
| JP | 2004538083 | 12/2004 |
| JP | 2008523910 | 7/2008 |
| JP | 2008531086 | 8/2008 |
| JP | 2014188214 | 10/2014 |
| WO | WO2006065949 | 6/2006 |
| WO | WO2010028090 | 3/2010 |
| WO | WO2012061657 | 5/2012 |

OTHER PUBLICATIONS

International Search Report dated May 15, 2012 from PCT Application PCT/US2011/059237.
Extended European Search Report dated Mar. 3, 2014 from European Application 11838841.2.
Office Action dated Oct. 24, 2014 from Chinese counterpart application 201180063931.0.
Office Action dated Oct. 16, 2015 from Japanese Application 2013-537842.
International Search Report and Written Opinion dated Dec. 29, 2016 from PCT Application No. PCT/US2016/055583.

* cited by examiner

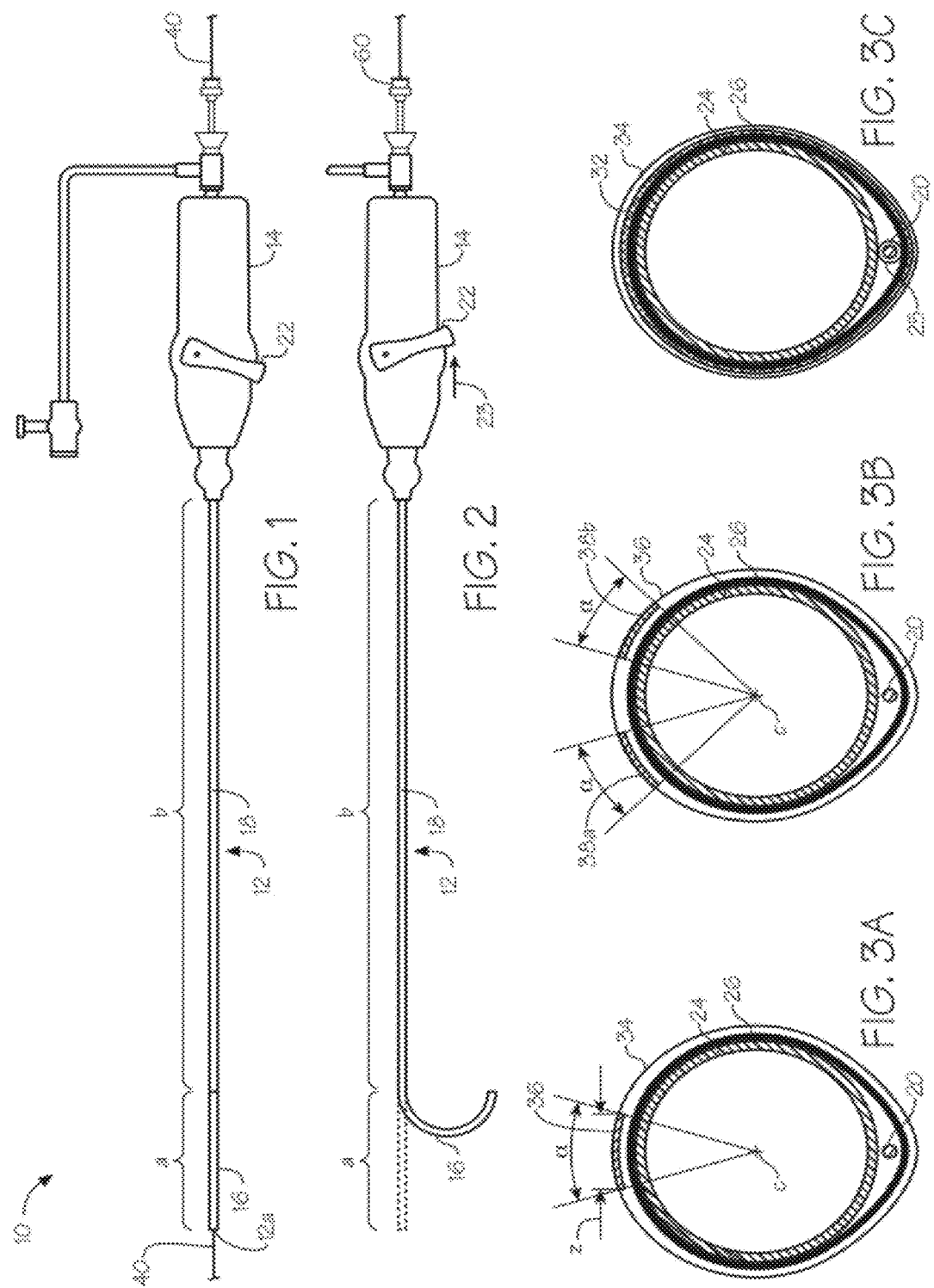

FIG. 3D1
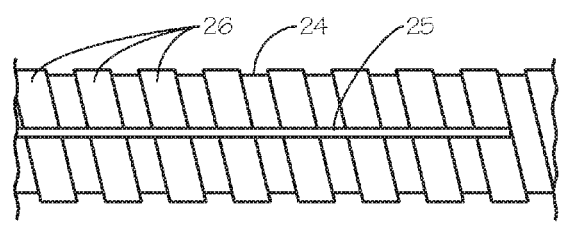
FIG. 3D2
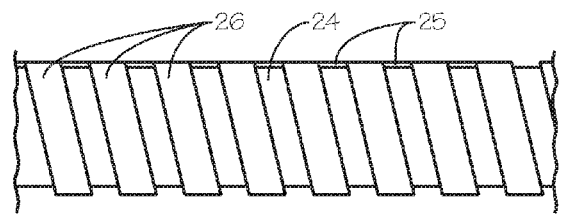

FIG. 4D1

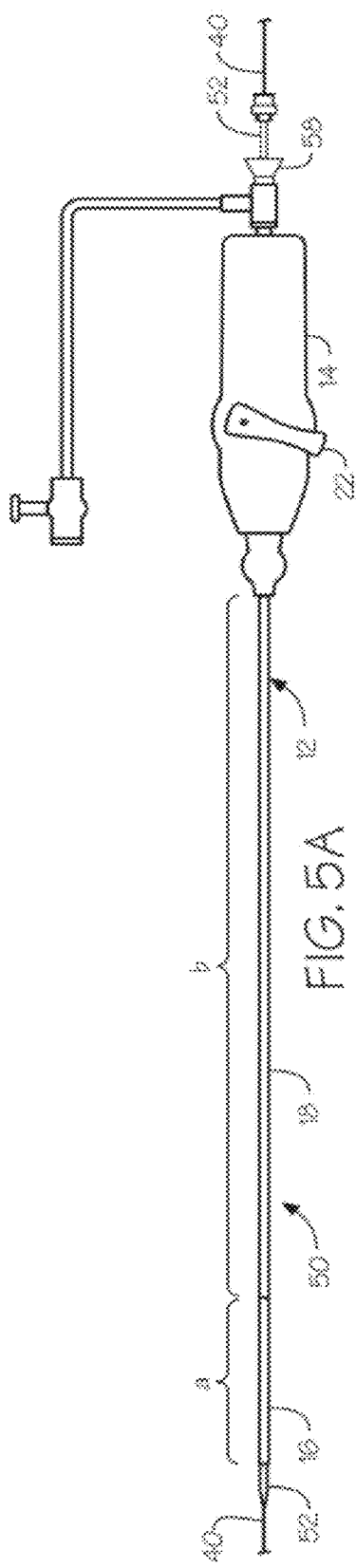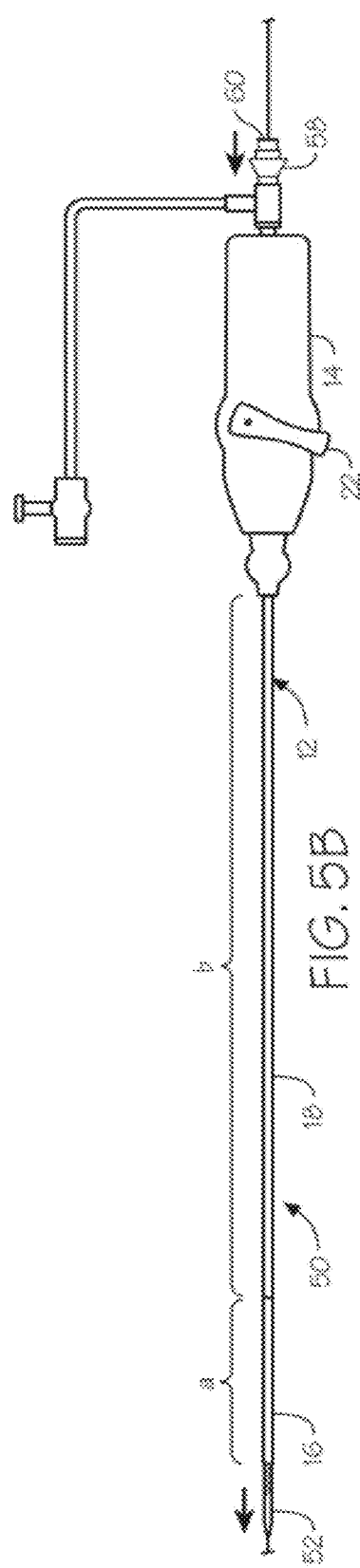

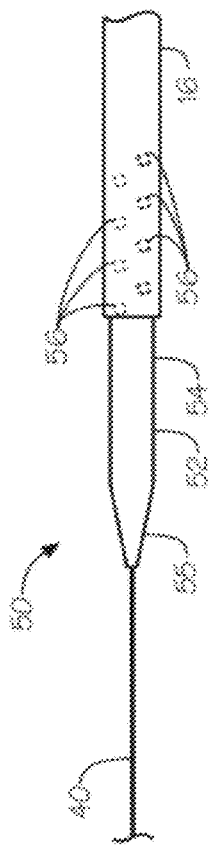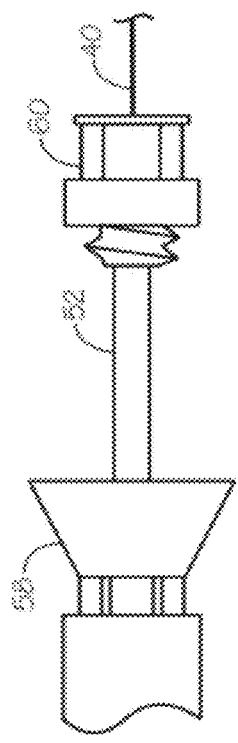
FIG. 6A
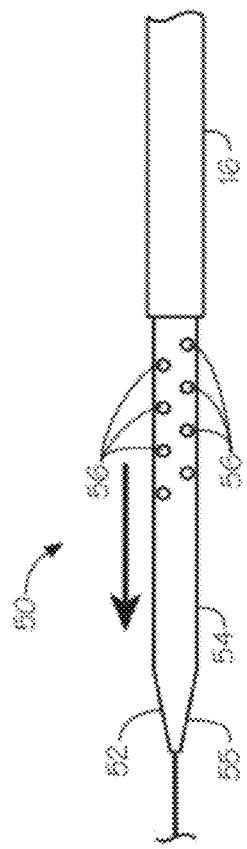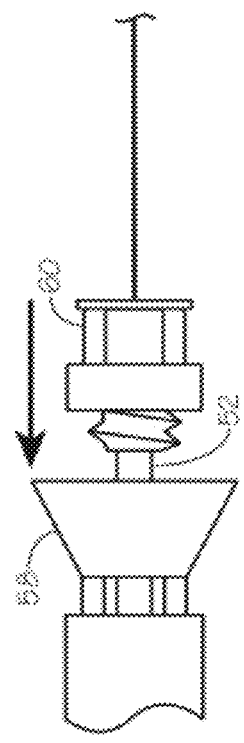
FIG. 6B

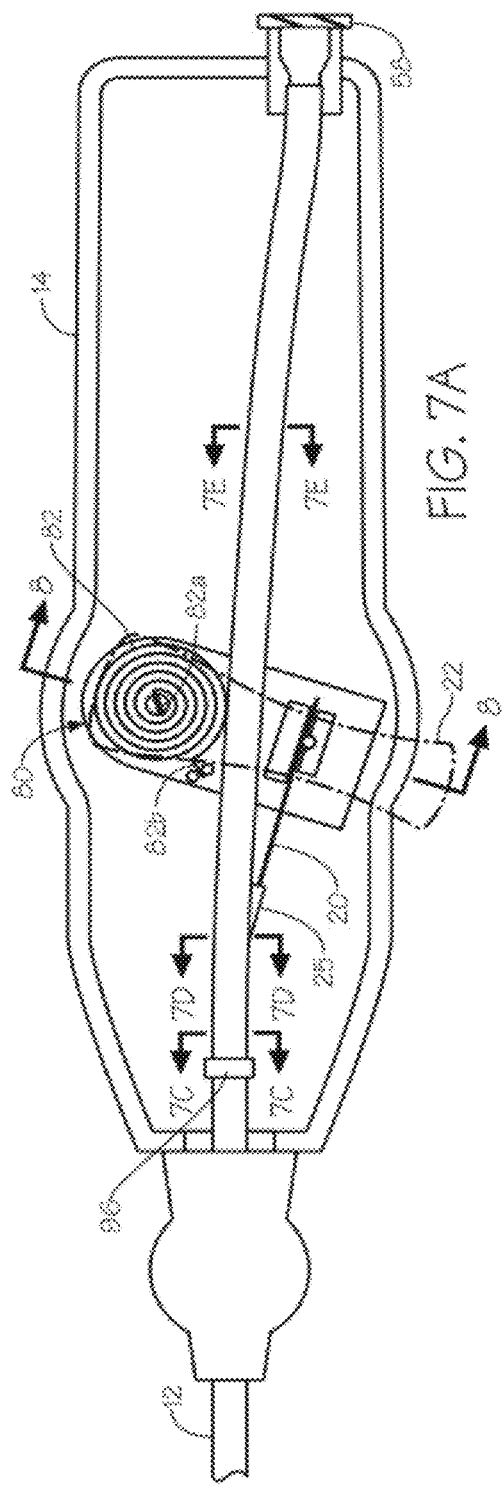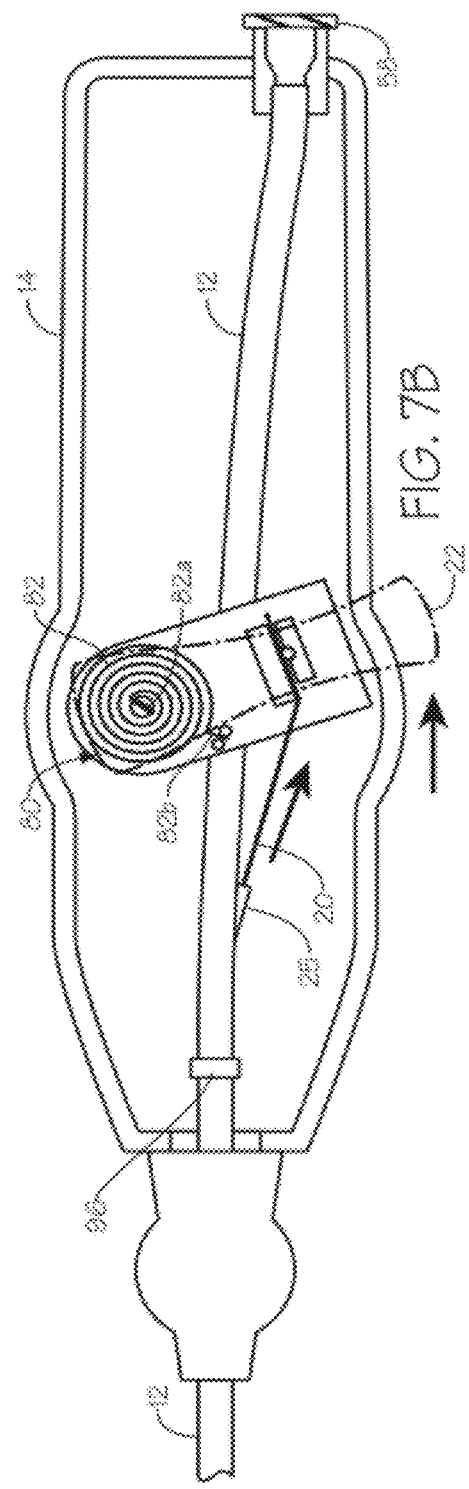

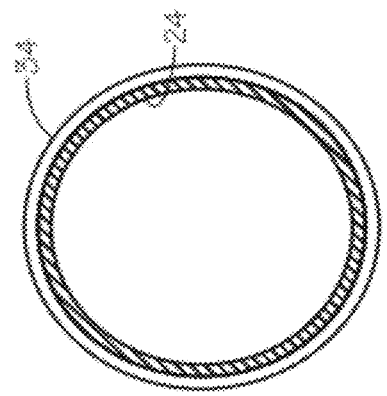
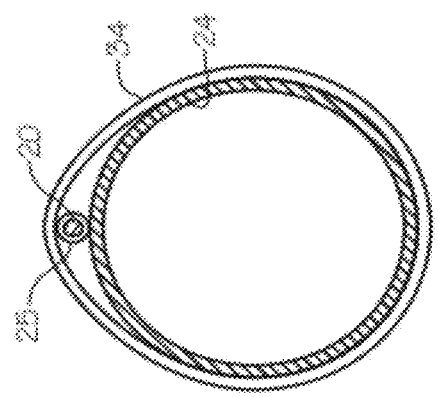
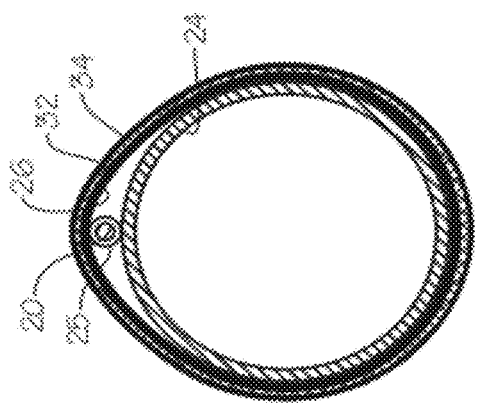

STEERABLE ENDOLUMINAL DEVICES AND METHODS

This application claims priority to Provisional Patent Application 61/409,929 filed Nov. 3, 2011.

FIELD OF THE INVENTION

The invention relates to steerable endoluminal devices including steerable introducers and guiding catheters.

BACKGROUND OF THE INVENTION

Steerable guide catheters provide a number of advantages over fixed guide catheters. Steerable guide catheters reduce procedural time. Because physicians can shape the device in real time to conform to the patient's anatomy they can quickly achieve the access they would like and enable the guide catheter to conform to the presenting anatomy. This prevents physicians from exchanging guide catheters to find one which works and such exchange involves additional product costs for each device, takes more time, and increases procedure risk as physicians manipulate more devices within patient anatomy.

Steerable guide catheters also provide more control. More control with such devices should equate to better outcomes as well. This is well described in the literature for carotid access. Carotid stenting trial data suggests that 40 percent of the strokes in these trials are due to emboli dislodged in the non-target vessel. This suggests that the manipulation which occurs during carotid access in the aorta is responsible for this—and thus responsible for 40% of the strokes which occurred. This is significant as other aorto ostial manipulations with fixed catheters are very similar to this. A steerable guide catheter that requires less manipulation to gain access to the target vessel and does not scrape the arterial wall as its curved portion is dragged along and flipped within the vasculature as it goes in straight over a wire is likely to significantly improve patient outcomes through more control and increase patient safety by limiting manipulations. Radial and brachial artery access using steerable endoluminal devices for cardiac and peripheral procedures is highly desirable due to the significant cost savings that would result from such procedures as compared to procedures performed via femoral access.

As devices can be advanced straight into the vascular space and then deflected to conform to a shape, they enable the distal end to have superior back up support in its deflected configuration than one can achieve with any sort of preformed catheter which must have a very flexible distal end as in its advancement and retraction within the vasculature, as a pre-shaped guide, it is likely to scrape the arterial wall and if too stiff could cause damage.

Steerable guide devices can be customized to the presenting anatomy; a physician can have exactly the desired curve shape and not aim for something in his current inventory that is close to the presenting anatomy. If a second catheter device (wire, balloon, atherectomy device, CTO device, stent etc.) inserted through a steerable introducer or steerable guide device changes the shape of the latter device it may be formed with the other device in place to provide the exact shape desired. This is not possible with fixed guides.

The difficulty in designing and manufacturing such devices is that the mechanisms to enable steering are complex and require real estate for their engineering. This adds a requirement of increased thickness to the catheter walls. Increased catheter wall thickness is a significant disadvantage as it requires a larger hole and larger access vessel to do procedures for a given therapeutic device such as a filter, wire, balloon, stent, coil, vascular graft, atherectomy, lasers, valve, snare, aspiration catheter or drug delivery system. The complexity of the mechanism also adds to the cost of the devices which compete with standard fixed guide shapes which have become a commodity. For these reasons, these devices are new in the marketplace.

These same issues are relevant for steerable introducers or steerable sheaths that enter the body percutaneously and do not require external introducers such as a guide or a steerable guide catheter does. A steerable introducer adds additional design requirements in that it must be more trackable and flexible to navigate tortuous anatomy like a sheath, but must have column strength to support the forces applied by pull wires or tendons used to deflect the deflection mechanism, and it must be able to transmit torque, which most sheaths do not do well, to enable it to be used to guide interventions with its shapeable distal end. Additionally, with the increasing demand in interventional cardiology for specifically shaped devices for accessing the coronary arteries, carotid artery, renal arteries, the atria and ventricles of the heart, femoral arteries and the like, a steerable introducer with preformed shape to enable such access would be highly desirable.

There remains a need to improve steerable endoluminal devices.

SUMMARY OF THE INVENTIONS

The devices and methods described below provide for a steerable endoluminal device adapted for delivery into a patient's vasculature. The device includes a tubular member having a proximal end and a distal end, the tubular member having a distal deflection portion that extends to the distal end and a main body portion that extends from the deflectable portion to the proximal end, the tubular member further including a stiff portion extending along the distal deflection portion, the tubular member comprising polymeric material circumferentially adjacent to the stiff portion, and the stiff portion comprising a material that has an elastic modulus that is greater than the elastic modulus of the polymeric material circumferentially adjacent thereto; and a pull wire extending between the proximal end and the distal end of the tubular member and having first and second ends, the first end being secured to the distal deflection portion to control deflection of the distal deflection portion of the tubular member.

According to another aspect of the invention, there are provided multiple methods for radial, brachial, or femoral access to various anatomical regions to treat patients presenting any of the several cardiovascular complications.

BRIEF DESCRIPTION OF THE DRAWINGS

FIG. 1 is a diagrammatic illustration of a steerable system according to one embodiment of the invention.

FIG. 2 is a diagrammatic illustration of the system of FIG. 1 with its deflection tip deflected.

FIG. 3A is a sectional view taken along line 3A-3A in FIG. 3

FIG. 3B shows a variation of the embodiment shown in FIG. 3A.

FIG. 3C is a sectional view taken along line 3C-4C in FIG. 3.

FIG. 3 is a longitudinal sectional view of the tubular member illustrated in FIG. 1, while FIGS. 3D1 and 3D2 show details of the distal deflectable portion of FIG. 3.

FIG. 5A diagrammatically shows the steerable system of FIG. 1 in combination with a dilator according to another embodiment of the invention.

FIG. 5B diagrammatically illustrates the embodiment of FIG. 5A with the dilator extended for discharge of fluid.

FIG. 6A is an enlarged view of the system illustrated in FIG. 5A.

FIG. 6B illustrates the system of FIG. 6A with the dilator not quite fully extended.

FIG. 7A diagrammatically illustrates a deflection actuator in the handle depicted in FIG. 1 according to one embodiment of the invention.

FIG. 7B diagrammatically illustrates the deflection handle of FIG. 7A with the actuator manipulated to deflect the distal end portion of the steerable system.

FIGS. 7C, 7D and 7E are cross sections taken along lines 7C, 7D and 7E of FIG. 7A.

DETAILED DESCRIPTION OF THE INVENTION

Figure 3:
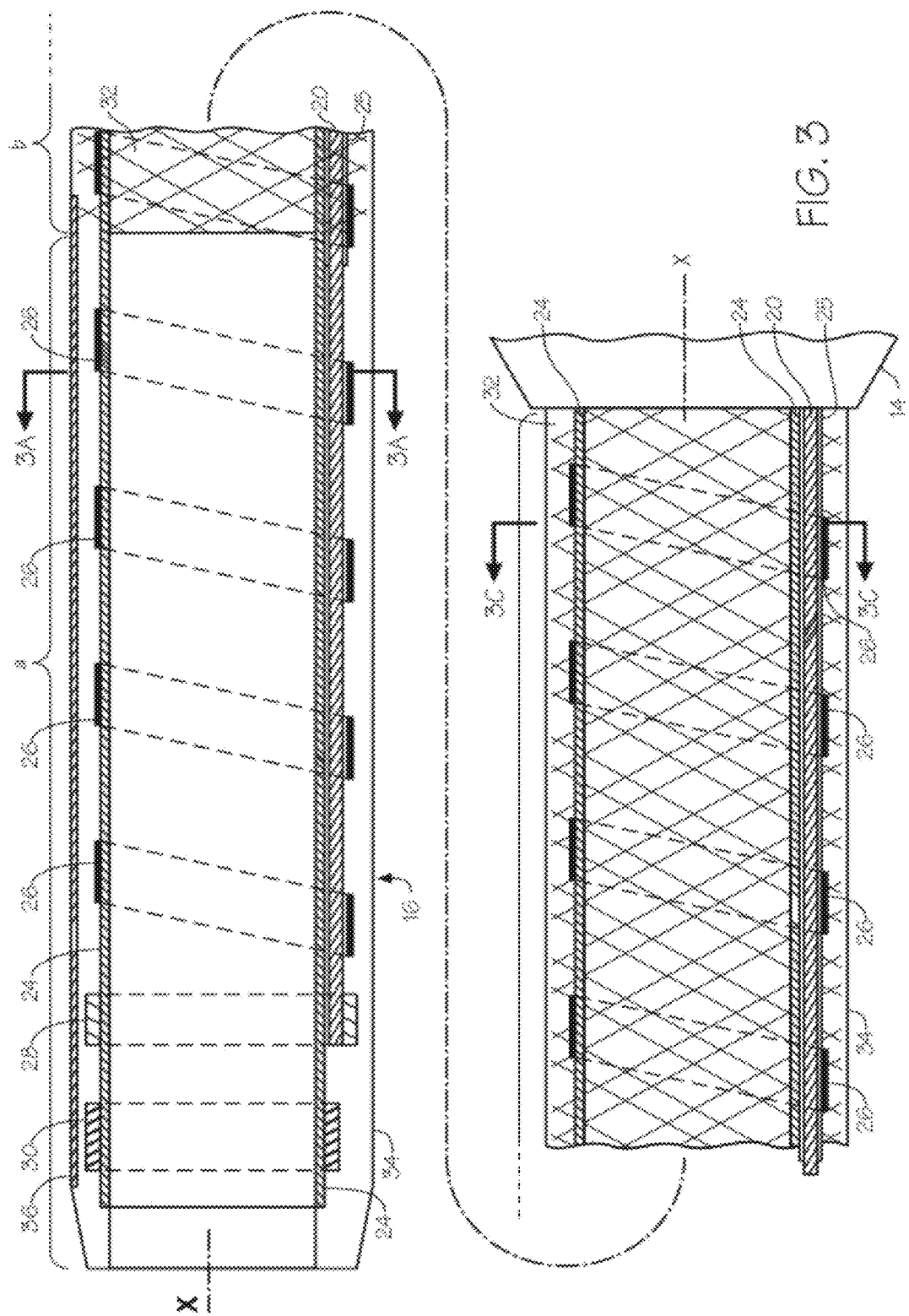

Steerable access devices that facilitate interventions that are difficult to perform using conventional systems are described below. Guiding catheter shafts are typically polymers with embedded metal braid as they need to transmit torque to a pre-shaped distal end. Percutaneous access sheaths are typically coil-reinforced as they need to be flexible, kink resistant, and trackable. According to one embodiment of the invention disclosed herein is a catheter shaft that combines the utility of each of these features and maintains a wall thickness of less than or equal to 0.5 mm (0.020"). According to some embodiments of the invention, steerable introducers with preformed shapes are described for certain specific interventional procedures.

FIG. 1 illustrates a steerable endoluminal system 10. Steerable system 10 is steerable introducer sheath as will be described in more detail below. Steerable system 10 generally comprises steerable tubular introducer sheath 12 having distal end 12a and proximal end 12b. Handle 14 is mounted on proximal portion 19 (see e.g., FIG. 4G) of catheter or introducer sheath 12 distal to proximal end 12b. Steerable introducer sheath 12 has a distal deflectable portion or segment, which extends a length indicated with bracket "a," and a main body portion or segment 18 which extends a length indicated with bracket "b." Main body portion 18 of introducer sheath 12 extends to proximal portion 19 of catheter 12, which extends through handle 14 and terminates at catheter or introducer sheath proximal end 12b (see e.g., FIG. 4G).

Distal deflectable portion 16 has one end that corresponds to distal end 12a and a second, proximal, end that merges into main body portion 18 or from which main body portion 18 extends. The distal end 12a consists of a soft tip of Pebax® polymer (a polyether-based polyamide). Distal deflectable portion 16 is operated through a pull wire 20 (FIG. 3) via steering lever 22, which is mounted on handle 14. As illustrated in FIG. 2, turning steering lever 22 as shown with arrow 23 bends distal deflectable portion 16. In the illustrative example, distal deflectable portion 16 is shown bent downwardly in FIG. 2 as compared to the straight configuration shown in FIG. 1.

Referring to FIG. 3, a longitudinal partial sectional view of steerable introducer sheath 12 is shown illustrating the different constructions of distal deflectable portion 16 and main body portion 18 and other components of the catheter. In the embodiment illustrated in FIG. 3, steerable introducer sheath 18 includes an inner tube 24, pull wire tube 25, which forms a lumen for receiving pull wire 20, helical ribbon coil 26, braid 32, and tubular outer jacket or cover 34. FIGS. 3D1 and 3D2 show details of the distal deflectable portion of FIG. 3, including the inner tube 24, the pull wire tube 25, and the helical ribbon coil 26.

Inner tube 24 can be made from any suitable material such as PTFE or other thermally resistant lubricious material such as those provided commercially by Zeus, Inc. In the illustrative example, inner tube 24 runs the length of introducer sheath 12. Pull wire tube 25 runs substantially parallel to inner tube 24 and extends from the proximal end of inner tube 24, which corresponds to the proximal end of 12b of introducer sheath 12, to a location just beyond main body portion or segment 16 and into distal deflectable portion or segment.

Pull wire tube 25 can be secured to inner tube 24 with any suitable means such as glue.

A coil such as helical ribbon coil 26 is helically wrapped around inner tube 24 and pull wire tube 25 along the entire the length of main body portion 18 (main body portion 18 terminates at its proximal end at handle 14) except for a distal portion thereof where pull wire ring 28 and marker band 30 are located. As described above, main body portion 18 of introducer sheath 12 extends into a proximal end portion that extends into handle. The portion of shaft with the braid and coil are attached inside the handle by way of the retaining block 96 (See FIG. 7A) That is, helical ribbon coil 26 extends from inside handle 14 distally to a location just proximal to pull wire ring 28 at the distal end of the deflectable portion. Pull wire ring 28 typically is an annular ring, which can be a closed ring, and radiopaque marker band 30 also can be annular or ring shaped and can comprise a closed ring. Helical ribbon coil, which can be formed from 0.003"×0.010" 304 stainless steel ribbon, is helically wound over inner tube 24 and pull wire tube 25. Its ends can be constrained, for example, by heat shrink tubing during assembly to ensure that the coil does not unwind. Braid 32, which can be 0.001"×0.003" braid is then braided over this subassembly as will be described in more detail below so that the braid extends from handle 14 to the proximal end of distal deflectable portion or segment 16 as it is not provided in the distal deflectable portion or segment in this embodiment. The braid and coil combination provides kink resistance and desirable torque transmission to enable steerable system 10 to be used as an introducer sheath for maneuvering around tortuous anatomy or a guide system. The braid and coil assembly also allows construction of a thin walled catheter having a wall thickness of ≤0.5 mm. In extreme bending, the radial strength of the coil supports the braid that would otherwise collapse and/or kink.

In one variation of the coil-braid combination described above, an asymmetric braid can be used incorporating some fine wires and some heavy wires, delivering hybrid braid/coil performance in a single process. For example a heavy wire such 0.003"×0.010" coil ribbon, could be wound in one direction while a fine wire such as 0.001"×0.003" braid wire could be wound in the other direction while being woven under and over the coil wire in an alternating pattern. In this variation, the process would utilize fewer braiding heads than normal, which typically involves 16, 24, or 32 heads, or odd numbers of heads such as 5 or 7 with some fine and some heavy elements. The heavy wire would act as a coil ribbon, adding kink resistance, and the fine wire would provide greater pushability and torque transmission.

Returning to FIG. 3, tubular outer jacket or cover 34 is applied to or over inner tube 24, helical coil 26, and braid 32 to provide a smooth catheter or introducer sheath outer surface and a catheter or introducer sheath with desired mechanical characteristics as will be described in more detail below. For example, outer jacket can be fused to inner tube 24, helical coil 26, and braid 32.

Outer jacket or cover 34 can be made from one or more materials, a polymer of varying durometer, or a plurality of polymers of varying durometer to provide, for example, better pushability in the proximal end and improved trackability in the distal end. In order to provide these characteristics, the outer shaft can be made from one or more tubes. The proximal tube would be a stiffer material or higher durometer than the distal tube. A tube with stiffness that is between that of the proximal and distal tubes may also be used between these two tubes in order to provide a smooth bending transition.

The shaft of the catheter can be considered a composite beam in bending. The jacket materials act as encapsulation matrix, and the braid acts as a strengthening fiber inside the matrix composite. The orientation of the fibers creates non-homogeneous strength characteristics. The stiffer the matrix materials, the higher the rigidity of the beam in bending. Along the length of the beam, differing materials can be used to fuse into the composite resulting in differing stiffness along the length. In endovascular products, it is common to desire that the distal end of the device is flexible and soft to be steerable and atraumatic, and the proximal end is stiff to increase the "push & torque" enhancing control. In between the distal and proximal, smooth transitions are desired to reduce the tendency to kink at the transition zone.

In the embodiment illustrated in FIG. 3, outer jacket or cover 34 includes a longitudinally extending relatively stiff portion, stiffener, or spine 36 that extends longitudinally along distal deflectable portion or segment 16 and a short distance (e.g., 0.25 inch) into main body portion or segment 18. The rigid polymeric spine extends into the jacket to bridge the materials. The bridged materials act to distribute loading in bending and tension to prevent separation of the materials at that point (from repeated deflection). The spine does not extend distally into the distal soft tip, however the PTFE liner does. The spine terminates proximally near the transition between the deflectable portion and the main body, and does not extend significantly in the main body. The spine's primary function is to keep the deflection zone from buckling when it is deflected with a stiff device inside. Stiff portion or spine 36 is stiffer than the remainder of outer jacket or cover 34. In one example, stiff portion or spine 36 is 72 D durometer (Shore D scale) PEBAX material throughout spine 36, the remainder of the jacket or cover 34 in distal deflectable portion or segment 16 is 35 D durometer PEBAX material, and the remainder of jacket or cover 34 in main body portion or segment 18 is 55 D durometer PEBAX material. That is, stiff portion or spine 36 is stiffer than the remainder of jacket or cover 34. Further, the portion of jacket or cover 34 that is in the region of main body portion or segment 18 is stiffer than the portion of jacket or cover 34 that is in the region of distal deflectable portion or segment 16 which is external to stiff portion or spine 36. It also should be understood that the durometer of these regions can be in a range of values. For example, outer jacket or cover 34 can comprise PEBAX material where stiff portion or spine 36 can have a durometer of 50 D to and including 90 D, the remainder of the jacket 36 in distal deflectable portion or segment 18 can have a durometer of 25 D to 55 D, inclusive, and the remainder of jacket or cover 34 in main body portion or segment 16 can have a durometer of 55 D to 90 D inclusive.

The polymeric stiff portion or spine 36 has a higher bending rigidity along its long axis and a lower bending rigidity along it short axis, which sets up a preferred and repeatable deflection that can be oriented with respect to the pull wire attachment. The longitudinal axis position of the pull wire determines the primary direction of deflection. Stiff portion or spine 36 typically has a longitudinal axis that extends parallel to the longitudinal axis X-X of steerable introducer sheath 12 (or the center line of inner tube 24) and is circumferentially spaced from the longitudinal axis of pull wire tube 25 or pull wire 20 by about 120 to about 240 degrees, more typically by about 180 degrees (e.g., 180 degrees) (see e.g., FIG. 3A). This configuration allows the relative spine rigidities described above and allows distal deflectable portion or segment 16 to be repeatedly deflected in the plane of the longitudinal axes of stiff portion or spine 24 and pull wire 20, while minimizing or eliminating twist of portion 16 as pull wire 20 is drawn. Such planar movement of the distal deflectable portion enhances deflection control and guidance of the device.

As described above, placing a polymer spine that has a relatively higher degree of rigidity (higher durometer) within the outer jacket of a relatively lower rigidity polymer (lower durometer) enables the spine to define the direction for bending without separate material being included. This has advantages in that it provides a simple polymer part which may be fused with other polymer materials and does not have significant material costs. Such a two part polymer outer jacket can also be formed cheaply by co-extrusion of the two materials and then cut to length for assembly. Previous deflectable catheters (e.g. BioCardia catheters) have used machined nitinol tubes to achieve the proper deflection axis. Using a coextruded polymer spine simplifies and significantly reduces the cost of the device.

The outer tubular jacket or cover 34 may comprise a plurality of polymers that are coextruded over inner tube 24, helical coil 26, and braid 32. This construction has many advantages as compared to previous deflection catheter constructions. For example, polymer spine 36 can be coextruded with the jacket 34 to achieve the desired deflection axis. Coextruded jackets are made as a single part which has a transverse cross section with the desired composite characteristics. The previous paragraph describes an assembly of multiple components to create the desired performance. This avoids the need for an additional stiffening component because spine 36 can be made from a polymer that is compatible with the remainder of outer tubular jacket or cover 34 and therefore it can be easily and reliably processed through heat fusing. Compatible materials in this context refers to those that can be coextruded together, that will bond together such that when actuated in use, they will not split apart. It is often desired that coextruded polymers are of similar melt temperatures for this reason. Materials like metal wires etc., that will not melt need to have a texture or mechanical lock so that they can be maintained in the extrusion matrix. Different polymers may be used, but having them all Pebax® is preferred because this is most likely to create a strong bond. In contrast, known deflectable catheters have used additional stiffening components including machined stainless steel or nitinol tubes to achieve the desired deflection axis. Previous deflectable catheters (e.g. deflectable catheters made by BioCardia, Inc., the assignee of the present application) have used machined nitinol tubes to achieve the proper deflection axis.

Stiff portion or spine 36 can comprise any suitable material such as the PEBAX material described above. Other materials that can be used include nylon, urethane, and PEEK. Stiff portion or spine 36 can be made from a thermoset polymer formulated to function with a softer material (e.g., where stiff portion or spine 36 is formed as an elongated section of polyimide material that is thermoset, perforated, and thereafter encapsulated in 35 D PEBAX to form the distal section of outer jacket 34 such that the PEBAX passes through the perforations and surrounds the spine.

Other materials that can be used in deflectable portion 16 external to spine 36 include other elastomeric materials that are softer than the spine such as urethane.

Referring to FIG. 3A, stiff portion or spine 36 has a transverse cross-section that extends circumferentially about inner tube 24 or outer jacket or cover 34 where the transverse cross-section defines an arc subtending an angle α of about 5 to about 120 degrees, more typically, about 10 to about 90 degrees, and preferably 34 degrees. Although a single stiff portion or spine 34 is shown in FIG. 3A, a plurality of stiff portions or spines can be used. In one variation illustrated in FIG. 3B, two stiff portions or spines 38a and 38b are used. Each stiff portion or spine 38a and 38b can have the same construction and subtend the same angle as stiff portion or spine 36. They typically will be symmetrically arranged about the longitudinal axis of pull wire 20 and be circumferentially spaced from one another by an angle which is the same as the angle which each stiff portion or spine 38a and 38b subtend as shown in FIG. 3B. In this manner, the distal deflectable portion or segment can be deflected in the plane of the longitudinal axis of stiff portion or spine 20 and the center line "C" of inner tube 24, while minimizing or eliminating twisting of the distal deflectable portion or segment during bending as pull wire 20 is drawn proximally.

Stiff portion 36 may comprise a metal (e.g., nitinol) insert, which can be in the form of a tube, that is embedded in a slot formed in polymer tubular outer jacket or cover 34 to provide differential bending rigidity. Differential bending rigidity, also referred to as preferential bending rigidity, means that less force is necessary to bend a member in one direction than in another direction. By providing higher bending rigidity in one quadrant of the cross section of the tube than another, the plane in which the device tip deflects can be controlled. For example, by including a stiffening member in the quadrant opposite the pull wire, the tube will preferentially foreshorten in the pull wire quadrant and bend so that the pull wire is on the inside of the curve. In yet another variation, polymeric deflection tubes comprising a flat wire in the spine by co-extruding or insert molding the flat wire within the spine, or alternatively laminating the flat wire in place using a commonly used heat shrink technique are used to enable differential bending rigidity. Other methods of forming the stiff portion or spine in the polymer composite include using coils with a welded spine element or zigzag elements with the crowns of zigzag elements welded intermittently, or injection molded plastic stent-like elements. In the example where coils with a welded spine are used, the distal deflection portion comprises a helical coil embedded in the tubular outer jacket or cover 34. The coil comprises a plurality of turns and a connector connecting adjacent turns. In this embodiment, the connector(s) form a portion of said stiff portion. For example, if the coil comprises three turns, the weld between the first and second turn forms a first connector and the weld between the second and third turn forms a second connector where the first and second connectors together with the coil portion therebetween form the spine.

The guide sheath may be constructed without the braid, but with the coil 26 shown in FIG. 3. This variation is suitable for procedures requiring better trackability (e.g., neurological access). Another variation of the guide sheath of FIG. 3 is constructed without coil 26, but with the braid. This variation is suitable for procedures requiring better pushability and/or column strength (e.g., percutaneous valve replacement).

This can be utilized with various distal deflection segments such as polymer spines, polymer deflection tubes, nitinol deflection tubes, or even flat pull wires that create the differential bending rigidity in the device. The combination of a thin walled deflectable guiding catheter and deflectable guiding sheath with a hybrid coil shaft design brings together the shaft construction of straight sheaths that are highly trackable and kink resistant with the torque control required of the guide feature which is realized on demand by deflecting the distal end of the catheter to take a desired shape.

A method of constructing the steerable introducer sheath of FIG. 3 will now be described. Referring to FIG. 4A-M, the steps for manufacture of such a steerable device with a compressed coil covered by braid will be described. The inner tube, pull wire tube, ribbon coil, and braid are trimmed to form the corresponding elements depicted in FIG. 3.

Figure 4A:
FIGS. 4A, B, C, D, D1, E, F, G, H, I, J, K, L, and M diagrammatically illustrate one method of assembling the device of FIG. 3.

FIG. 4A shows a dual lumen tube made of PTFE or other thermally resistant lubricious material and comprising an inner tube precursor 24', and pull wire tube precursor 25', which can be glued together or alternatively may be formed as a dual lumen extrusion. A mandrel is inserted into the pull wire tube precursor 25', typically a 0.007" diameter rigid mandrel is inserted in a 0.008" inner diameter pull wire tube having a wall thickness of 0.001". A hard polymer beading material or stainless steel mandrel is inserted into inner tube precursor 24'. The beading material which may be a PTFE extruded rod or mandrel has an outer diameter that is the same as the desired inner diameter of inner tube precursor 24'. The inner diameter of inner tube precursor 24' and, therefore, inner tube 24 typically is 0.010 in. to 0.394 in. (0.25 mm to 10 mm.)

Figure 4B:
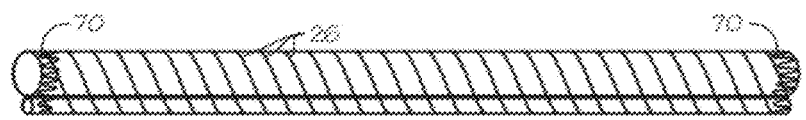

Referring to FIG. 4B, a shaft coil or a ribbon is helically wound over inner tube precursor 24' and pull wire tube precursor 25' assembly to form a helical ribbon coil or shaft coil. In this example, the ribbon is a 0.003" thick×0.10" wide 304 stainless steel flat ribbon. The helical coil is wound with a coil winder as is known in the art and the ends of the helically wound ribbon coil or shaft coil are then constrained, for example by heat shrink tubing 70 made of polyolefin material to ensure that the coil does not unwind or alternatively, by using tape to secure the ends.

Figure 4C:

Referring to FIG. 4C, braid such as 0.001×0.003" braid is then braided over the inner tube, pull wire tube, ribbon coil subassembly. This may be made in a continuous process or in discrete lengths as is known in the art.

Figure 4D:
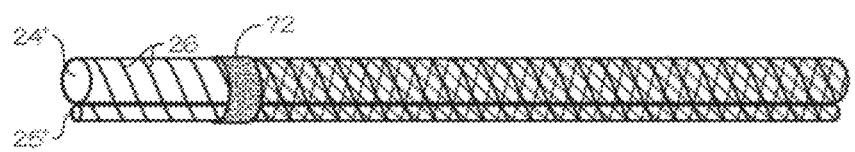
Figure 4E:
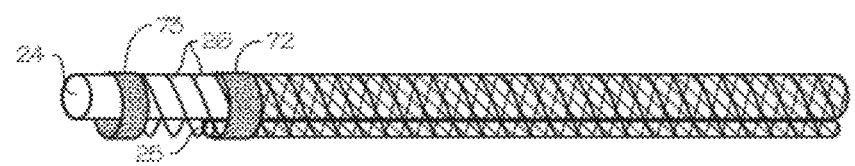

Referring to FIGS. 4D and 4E, thermal heat shrink PET mask 72 is a different version of a shrink tube with a very thin wall. This PET mask 72 is used in conjunction with a fused "bracelet" of Pebax® to fix the braid at its distal end 72. The PET mask is applied to the proximal end (FIG. 4D) and distal end (FIG. 4E) of the braided-coil subassembly to stabilize the proximal and distal ends of the braided-coil subassembly after which a proximal portion of the braid is trimmed or removed (FIG. 4D) and then the portion of the braid in the distal deflectable portion 16 is trimmed or removed and a distal portion of the coil trimmed or removed to form the construction shown in FIG. 3 (FIG. 4E) to prepare them for subsequent operations described below. A distal portion of pull wire tube precursor 25' also is trimmed or removed just distal to the deflection zone. The proximal end extends past the end of the braid/coil to "exit" from within. To join the handle deflection mechanism ("crank"). The outer jacket is melted around the exiting pull wire lumen to create a pressure and aspiration seal in this location FIG. 4D1 illustrates an embodiment wherein a section of the pull wire tube 28 is manually twisted around the inner tube 24 at a location within the main body portion or segment 18

Figure 4F:
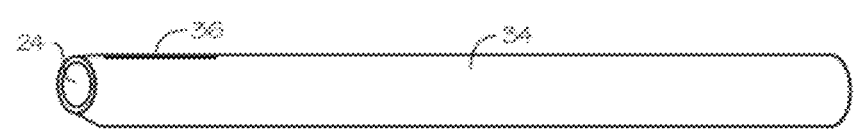

FIG. 4F shows application of material to form a portion of tubular outer jacket or cover 34. In one embodiment, jacket 34 is made entirely from one material. This is accomplished by cutting a longitudinal slot out of jacket 34, replacing it with a stiffer material, and heat fusing it into place. A spine can be placed underneath this jacket which is bonded/impregnated into the outer jacket tube when the jacket is laminated to the inner assembly. If entirely one material, it is simply standard extrusion methods. If more than one material as in our case, then there needs to be a special metering process to inject a "stripe" of a different material (in this case higher durometer) into the extruder crosshead at a specific portion of the circumference.

Alternatively, polymers of varying durometer may be utilized to achieve, for example, better pushability in the proximal end, and improved trackability in the distal end. The jacket is fused to inner tube precursor 24', pull wire tube precursor 25', ribbon coil 26, and braid 32 through any suitable means such as lamination to form a portion of outer jacket 24 having a 55 D PEBAX section for the jacket portion proximal to distal deflectable portion 16 (including main body portion 18), a 72 D PEBAX spine 36, and 35D distal deflectable portion outside of spine 36. During manufacture the raw tubing is extruded into a slightly oversized tube, then the catheter components are assembled (sliding the oversized tube over the top of the beading or mandrel, liner, and braid/coil) and the assembled components are "laminated" by using hot air and shrink tubes to cause the extrusion to collapse, melt, flow, and bond or encapsulate the components in the substrate assembly.

Figure 4G:
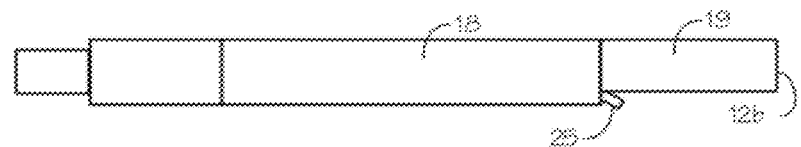
Figure 4H:
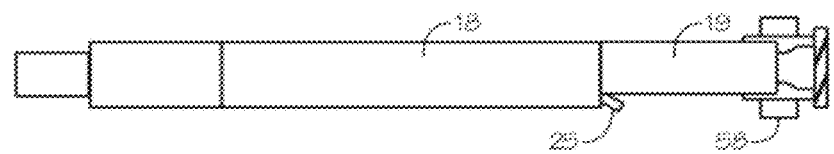

FIG. 4G shows trimming of a proximal portion of the ribbon coil, so that the coil does not extend into handle 14, lamination of the proximal jacket material to the inner assembly, lifting of the pull wire mandrel and laminating underneath it to form a joint which only has the pull wire mandrel exposed through the butt of the proximal lamination. In the preferred embodiment, all of these materials are 55 D PEBAX. After this lamination, the pull wire mandrel is removed.

Referring to 4H, a conventional luer 58 is attached to the proximal end of the subassembly shown in FIG. 4F, which end will form the proximal end 12a of catheter 12, using an adhesive such as acrylated urethane and cured with UV light.

Figure 4I:
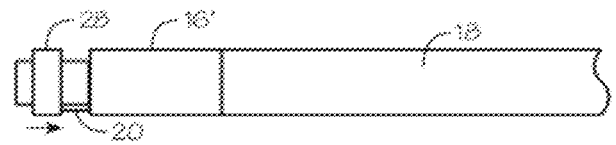

Referring to FIG. 4I, the pull wire mandrel is withdrawn and the pull wire assembly assembled. The pull wire assembly consists of a cylindrical metal pull wire ring 28 that is mounted on inner tube precursor 24' and laser welded to the distal end portion of metallic pull wire 20, which is passed through pull wire tube precursor 25'. In the preferred embodiment, metal pullwire ring 28 and pull wire 20 are made of 304 series stainless steel. (The pull wire attachment to the deflection portion is described in detail in U.S. Pat. No. 6,511,471 Rosenman, et al., incorporated by reference in its entirety herein).

Figure 4J:
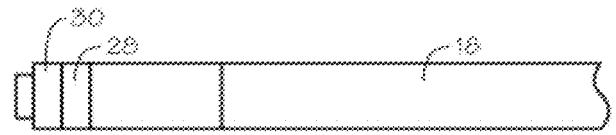

Referring to FIG. 4J, a marker band is placed over inner tube precursor 24'. The marker band is made from a radiopaque material such as platinum iridium. A band of, for example, 55 D PEBAX is then laminated over marker band 30 and pull wire to encapsulate it on inner tube precursor 24'.

Figure 4K:
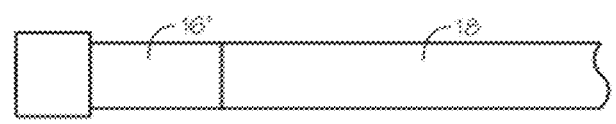
Figure 4L:
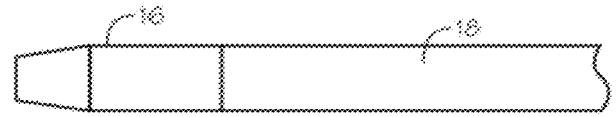

Referring to FIG. 4K, the distal end portion of inner tube precursor 24' is trimmed or removed to form inner tube 24 shown in FIG. 3 and a thin 55 D PEBAX soft tapered tip is laminated over marker band 30 and pull wire ring 28 and fused to the distal end of the PEBAX illustrated in FIG. 4G to form the portion 16' of distal deflectable portion 16 up to the end of pull wire ring 28. The soft tip is then tapered and cut to form distal end 12a of catheter 12 (FIG. 4L).

Figure 4M:
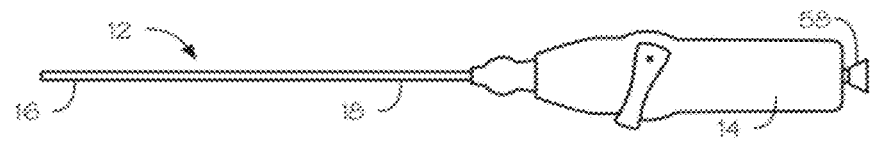

Referring to FIG. 4M, handle 14 is attached to the catheter or introducer sheath and the pull wire is set in the deflection mechanism so that it remains straight and so that when handle lever 14 is manipulated the pull wire applies a force along its length to the distal end of the catheter 12 causing the softer 35 D deflection zone to bend in a direction and geometry defined by the length of the zone and the shape and size of the polymer.

Such a catheter or introducer sheath 12 can be made with a wall thickness of less than 0.60 mm. In a preferred embodiment, the wall thickness is about 0.55 mm. In a yet preferred embodiment, the wall thickness is less than about 0.50 mm. In another embodiment, the wall thickness is about 0.30 mm. Further, this construction provides desirable kink resistance and torque transmission to enable it to be used as both an introducer sheath for tortuous anatomy but also as a guide system. This eliminates the need for larger external access sheaths which deflectable guides require, thereby providing significant advantages of making a smaller home in the vessel wall and enabling the introduction of standard interventional devices.

The inner diameter of the tubular member of the catheter or introducer sheath made as described above is within a range of about 4.5 F to about 9 F.

The tubular member of the catheter or introducer sheath will have a length of about 90 cm to about 130 cm.

Referring to FIG. 5A, the steerable system of FIG. 1 is shown in combination with a dilator to form an introducer sheath-dilator system 50. FIG. 5B illustrates the embodiment of FIG. 5A with dilator 52 extended for discharge of fluid such as imaging contrast fluid.

Referring to FIGS. 6A and 6B, dilator 52 comprises a tubular member 54 having a tapered distal end 55, and a plurality of fluid discharge openings 56. During delivery of introducer sheath-dilator system 50 to the target site, the dilator is in the retracted position shown in FIG. 7A so that openings 56 are hidden within the sheath to avoid any abrasion with the vessel lumen. After extending dilator 52 from introducer sheath 12 as shown in FIGS. 5B and 6B, imaging contrast fluid can be discharged from within dilator tubular member 54 through side openings 56 for anatomical imaging. In this manner, the need for an additional diagnostic catheter is eliminated.

Referring to FIG. 5A, floating luer hub 58 is slidably mounted on a reduced diameter proximal portion of tubular member 54. An annular step forms the diameter transition and stop 62 that stops further movement of luer hub 58 in the distal direction. A male luer hub 60 is fixedly secured to the proximal end portion of dilator 52. When luer hub 60 is moved distally as shown with the arrow in FIG. 6B, dilator tube 54 moves distally exposing dilator openings 56. When luer hub 60 is locked in female luer hub 58 (FIG. 5B, the introducer sheath or the dilator can be used to disperse contrast medium in the targeted region. The contrast medium is injected through the side port of the hemostasis valve or through the luer on the proximal end of the hemostasis valve.

Dilator 52 can be made with a distally extendable length. The extendable length has side holes that are manually exposed once percutaneous access has been gained. The dilator can have varying durometers along its length. The distal tip can be firm for skin penetration, soft segments provided in the remainder of distal deflectable portion 16.

Linear stiffness variation on taper (due to materials properties, a linear taper results in a non-linear stiffness change)

FIG. 7A diagrammatically illustrates a deflection actuator in handle 14 according to one embodiment of the invention and FIG. 7B diagrammatically illustrates the deflection actuator of FIG. 7A with the actuator manipulated to withdraw pull wire 25 and deflect the distal deflectable portion 16 of the steerable system as shown, for example, in FIG. 2.

Referring to FIG. 7A, deflection actuator 80 generally includes lever 22, which is pivotally mounted to handle 14, and a mechanism to limit force applied to pull wire 25, and lever 22. The force limiting mechanism comprises torsion spring 82 that provides a controllable, limiting force on pull wire retraction as shown with the arrows in FIG. 7B, which illustrates the actuator of FIG. 7A in a withdrawn or actuated state to deflect distal deflectable portion 16 (FIG. 2). However, it should be understood that other mechanisms can be used to provide such a limiting force on pull wire 25. FIGS. 7C, 7D and 7E are cross sections taken along lines 7C, 7D and 7E of FIG. 7A.

Figure 8:
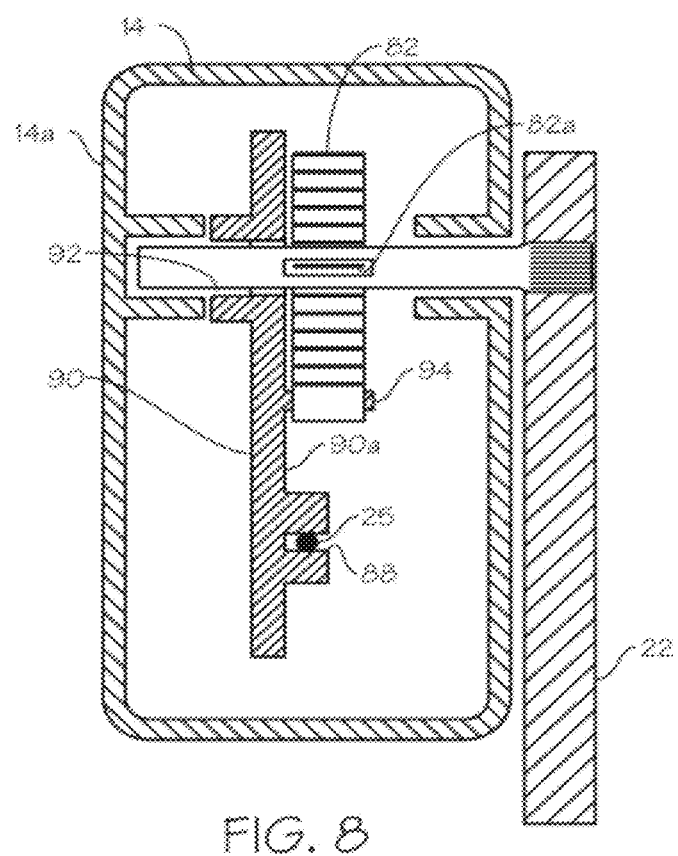
FIG. 8 is a sectional view taken along line 8-8 in FIG. 7A.

Referring to FIG. 8, lever 22 is pivotally coupled to handle 14 through pin 84, which has one end fixedly secured to lever 22 and another end rotatably mounted in cylindrical pin support 86, which extends from the housing 14a of handle 14 and can be integrally formed with the handle housing or a separate component that is secured to the handle housing. In this manner, the pin rotates in pin support 86 when lever 22 is pivoted or moved as shown with an arrow in FIG. 7B. Pull wire 25 is fixedly secured in slot 88, which is formed in crank plate member 90. Crank plate 90 has a through hole 92 through which pin 84 extends and is fixedly secured to crank plate such that crank plate 92 pivots when pin 84 rotates. Torsion spring 82, which comprises a spiral element, is mounted on pin 84 and has its inner end 82a fixedly secured in a slot in pin 84 and its outer end 82b (shown in FIGS. 7A and 7B) fixed to crank plate 90 through crank plate pin 94, which extends from base plate 90a of crank plate 90 and is integrally formed therewith.

As illustrated in FIG. 7A, pull wire is directly attached to crank lever 22

The pull wire is directly coupled to a crank assembly which actuates the deflection feature.

Among that many advantages of this construction is that it limits the amount of force applied to pull wire 25 including, but not limited to, minimizing wire failure due to excessive force, limiting deflection of the distal deflectable portion and its distal tip due to positional and/or directional limitation within a patient, and general safety to patient anatomy. In other words, this construction allows for actuation of crank 90 (and thus the pull wire) under normal force but limiting the force applied to the wire if excessive force is applied to lever 22. This is in contrast to systems which use a fixed couple between the pull wire and the crank lever, which provides direct application of force from finger actuation to the pull wire. This is to say that the finger knob is mechanically fixed to the crank, and the crank is mechanically fixed to the pull wire. In the illustrative embodiment, the force limiter ensures that the maximum stress on the catheter distal deflectable portion is controlled to minimize breakage of a limited strength deflection mechanism's actuation.

The torsion spring specifications define acceptable applied force with the spring not significantly engaging until a certain force is applied to the knob Another use of this design is as a safety feature such as when a deflected device is removed from a patient's tortuous anatomy, without first straightening the deflection zone. The spring relief can relieve the deflection zone by "breaking away" from the deflected position at a maximum stress so as not to destroy the catheter nor, more importantly, injure the patient's anatomy.

In other variations, the force limiting mechanism can use other spring types to functionally meet the desired goal of limiting tension applied to the pull wire. Further, although not illustrated, it should be understood that the force limiting mechanism can be used with other steerable catheters having a pull wire actuated deflectable tip.

The steerable systems can simplify procedures associated with peripheral access, enhance physician control, and thereby help improve clinical outcomes in treating peripheral artery disease or PAD. Between 8 and 12 million Americans suffer from PAD, which is caused by the accumulation of plaque in leg or foot arteries, reducing blood flow. Symptoms include leg pain when walking or at rest. PAD can lead to tissue loss and eventually limb amputation. An arterial access steerable conduit with a profile small enough to be used in routine PAD procedures and an inner lumen large enough to deliver the equipment used in treating PAD such as stents, atherectomy devices, laser systems, and balloons has resulted in these procedural advances. The important procedure of contralateral access in which a femoral access is used to cross the iliac bifurcation to work on the contralateral limb in peripheral artery disease (PAD) may be performed with a steerable introducer as described above and eliminate the need for three devices, which are typically used, and save a number of device exchanges that take time and add patient risk and cost.

The devices of the present invention provide a much needed alternative for interventionalists to treat patients because the steerable sheathless guide of the present invention have the novel features of small outer diameters coupled with structural rigidity sufficient to effectively navigate through tortuous anatomy without necessitating the use of a dilator. A preferred embodiment of the invention comprises a 5 F steerable sheathless guide with an outer diameter of 7 F. The device would have a lubricious coating along its entire length. The device would be provided with two dilators for compatibility with a 0.018 inch guide wire and a second one compatible with a 0.035 inch guide wire. Optionally, the dilators would also have holes along the distal tip in a spiral configuration to enable diagnostic imaging contrast infusion at the target site. Typically, the holes in the dilator would be smaller than the guide wire or roughly 0.0008 inches to 0.012 inches in diameter and there would be about 6 to about 8 holes on the portion of the dilator that protrudes from the distal end of the steerable endoluminal device which may be any one of a sheath, a guide or a sheathless guide.

One example of how introducer sheath-dilator system 50 reduces steps is provided below.

Following needle puncture and guide wire placement into an artery and without a steerable introducer sheath, the iliac bifurcation often is crossed with the following steps: (1) Introducer sheath is placed. (2) The introducer dilator is removed. (3) A diagnostic catheter is advanced into the artery to gain contra lateral access. This occasionally results in the selection of multiple diagnostic catheters and advancing them until limb access is achieved. (4) The wire is then removed from the patient. (5) Contrast dye is then injected through the diagnostic catheter. (6) In most procedures a stiff wire is then advanced through the diagnostic catheter and down into the contralateral limb. This is intended to serve as a support for a sheath which will support the ultimate intervention. (7) The diagnostic catheter is then removed. (8) The introducer sheath is then removed. (9) An interventional sheath (such as the Terumo Pinnacle Destination sheath or the Cook Ansel sheath is advanced over the stiff wire) across the iliac bifurcation and to a point in the anatomy that the device is stable. (10) The stiff wire is then removed. (11) A soft wire is then advanced through the sheath. Typically but not always the same wire that began the procedure for access. (12) The sheath with wire is then advanced to the position for the subsequent intervention often times with the wire protruding. (13) The dilator is then removed from the sheath. (14) Therapeutic devices such as CTO devices, balloon catheters, stent systems and debulking devices such as atherectomy devices are advanced. These can often be advanced over the same wire.

With the steerable introducer-dilator system 50, the same results can be achieved in much fewer steps than the current procedure. If necessary, predilation is performed followed by the following steps: (1) Steerable introducer sheath is placed with the dilator used to facilitate introduction into the vasculature. (2) The dilator is removed from the deflection zone of the sheath. (3) The steerable introducer is deflected down the contralateral limb. (4) Contrast dye is then injected through the steerable introducer. (5) The wire is advanced down the contralateral limb followed by the dilator and the steerable introducer sheath is relaxed. (6) The steerable sheath (now straight) with wire is then advanced to the position for the subsequent intervention often times with the wire protruding. (7) The dilator is then removed from the sheath. (8) Therapeutic devices such as CTO devices, balloon catheters, stent systems and debulking devices such as atherectomy devices are advanced. These can often be advanced over the same soft wire. This procedure eliminates steps and does not require an introducer, a diagnostic catheter, or a sheath—all of which are replaced by the single steerable introducer sheath with the dilator 50.

A method of crossing a curve with a steerable sheath-dilator system 50 also can be used for other applications including carotids and is similar to that described above regarding crossing the iliac bifurcation. Introducer sheath-dilator system 50 has other applications as well such as cardiac chamber access. Today there are a number of ways to get into the chambers of the heart. The right heart chambers are accessed for pacing, ablation, and biopsy procedures through venous access in the subclavian or cephalic veins or from the femoral veins in the groin. Most procedures today in the left side of the heart are the most complex and involve the use of other devices. Left atrial access through a transeptal approach is performed through the groin as the devices all have thick walls and cannot enter the heart through the radial approach.

Generally left ventricular heart access is performed using an arterial stick in the femoral artery in the groin and advancing a catheter retrograde across the aortic valve. A special catheter that can enter the left heart and then flip upwards to access the left atrium exists but most procedures today are performed through a transeptal puncture in which a catheter is advanced from the groin through the venous system and is used to puncture the atrium of the right heart to enable access to the left heart. Typically steerable guides or introducers are used to perform this procedure. The examples below illustrate the use of the devices described above to perform various procedures.

The following describes exemplary methods of using of steerable sheaths or introducer sheaths in further detail.

Example 1: Radial and Brachial Access for Coronary, Neurological and Peripheral Procedures Providing access from the arm has advantages in enabling patients to be discharged and mobile with only a bandage and no closure devices are necessary. In contrast, femoral access has higher costs associated with patient management as a closure device is often necessary and mobility of the patient is limited, resulting in the need of a gurney after a procedure which significantly delays discharge time of patient and thereby reduces the frequency and the number of patients treated.

Radial access for cardiac transendocardial delivery or left ventricular procedures:

A wire is inserted into the radial artery using a Seldinger technique. The steerable endoluminal device with dilator having an internal diameter of between 4 F and 5.5 F and an outer diameter of between 6 F and 7.5 F and having a lubricious coating on at least part of its distal length is inserted and advanced over a guide wire. At times, contrast may be infused through the dilator or the dilator may be removed and contrast may be infused through the device to assess anatomy roadmap. The device is advanced into the aorta and the dilator is removed. The steerable feature of the sheath may be used to guide the guide wire across the aortic valve, after which the guide sheath follows into the left ventricular chamber. The wire is removed and through rotation enabled by its torque transmitting ability and deflection of the distal segment a conduit that may be pointed towards any wall region within the left ventricle is enabled with an internal diameter (lumen size) of up to 5.5 F (1.8 mm), able to deliver transendocardial delivery catheters such as the 5.2 French BioCardia Helix Model #953 (Bio-Cardia, Inc., San Carlos, Calif.) or other catheters for cardiac mapping, ablation and the like.

Example 2: Trans-Atrial Septum Access

A steerable sheath with a long dilator is used for this application. A preferred embodiment of the invention suitable for this application comprises a steerable endoluminal device with an internal diameter of 6.5 F or 7.5 F or 8 F and an average wall thickness of less than 0.40 mm. The steerable sheath and dilator are advanced into the right atria from the femoral or brachial vein. The distal end of the sheath is deflected to point at the septum of the atrium and advanced until the dilator is situated against the septum causing the septum to tent. The deflection, advancement and placement of the dilator against the septum is observed and confirmed with the help of imaging technology such as echocardiography. After the dilator is confirmed to be in an acceptable position against the septum, a soft preformed flexible guide wire with a short sharp needle on the end is advanced through the dilator and into the left atrium. Alternatively, the guide wire is hollow for delivery of fluids into and through the sharp needle. In a slight variation to the above procedure, a second embodiment of the invention wherein the steerable device is a 7 F or 8 F sheath with an internal diameter of 7.5 F or 8.5 F and could also potentially be used to guide ablation catheters once advanced across the septum—or exchanged for larger introducers for other larger diameter technologies.

Example 3: Shaped Renal and Mesenteric Access Sheaths

Catheter based treatment of renal artery disease is another application of the devices of the inventions. In particular, a 6 F steerable sheath embodiment of the invention comprises a long preformed gentle curve such that the deflection of the distal element results in the device having back up support from the distal aorta. Devices generally used for treatment of renal artery disease are the renal double curve catheters. See *Vascular Medicine and Endovascular Interventions* by Thom W Rooke (Google Books). The embodiment of the invention most suitable for such use would comprise a preformed curved region in a shape that is substantially similar to a first curve of a renal double curve catheter (RDC1) and a distal second curve formed by the deflectable portion with a length of about 3 cm to about 5 cm wherein the deflectable portion is deflected around a tight radius of curvature of about 1 cm towards the proximal end of the tubular member continuing the RDC1 curve and within a plane defined by the preformed shape defining the first of the RDC1 curves.

Example 4: Carotid Access Using Steerable and Pre-Shaped Sheaths

Figure 9A:
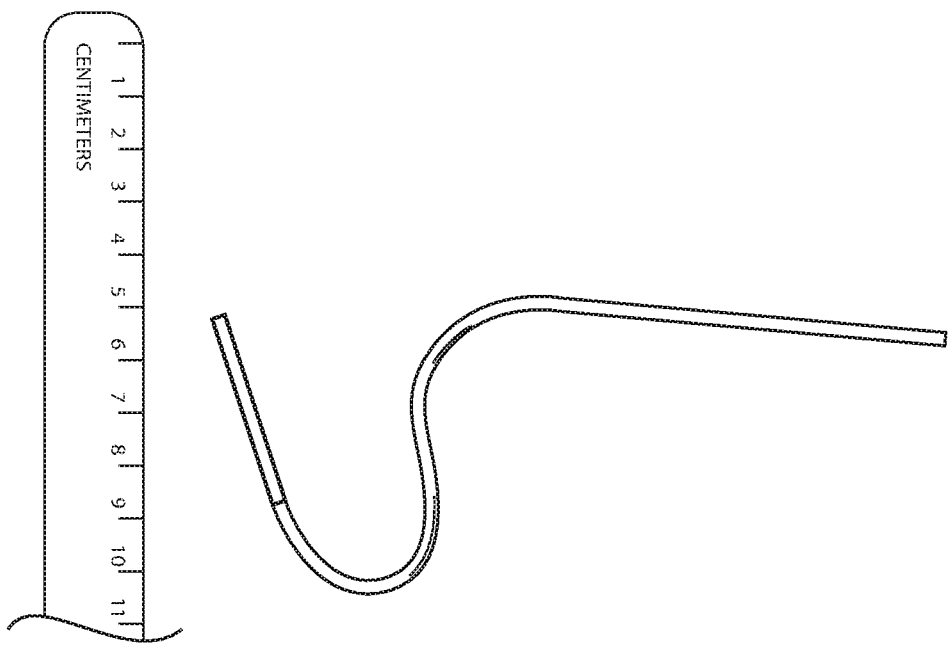
FIG. 9, Panels A and B illustrate preformed shape designs of various embodiments of the steerable sheaths of the invention.
Figure 9B:
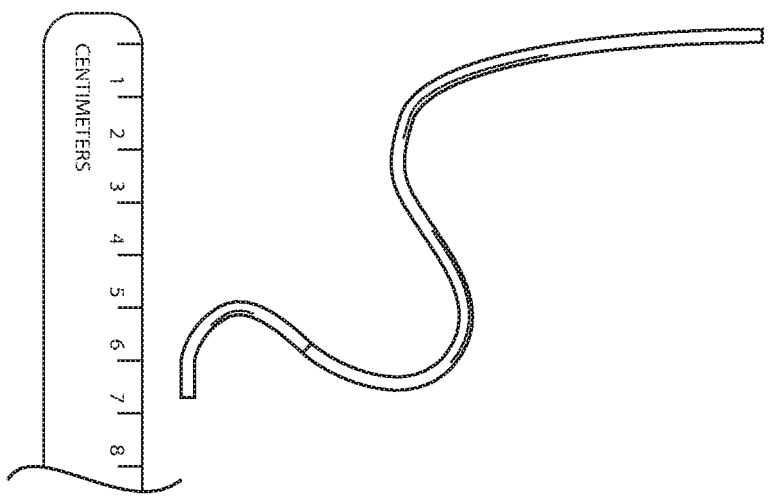

Careful manipulation when accessing the carotid is essential in order to avoid strokes caused by emboli dislodged in the non-target vessel. Carotid access is performed from either the femoral artery or a brachial artery in which a 180 degree turn is made to go up to the carotid. Generally two shapes with proximally located prefixed bends are used (such as the Vitek shaped catheter). In one embodiment of the present invention, steerable sheaths having a preformed shape are provided. The preformed shape is substantially similar to that of the Vitek catheter and the distal deflection portion has a length of about 3 cm to about 5 cm and when deflected, it deflects around a radius of curvature of about 1 cm away from the proximal end of the catheter and within the plane defined by the preformed shape (See FIGS. 9A and 9B). The unique combination of the preformed shape coupled with the deflection of the sheaths of the present invention are ideal for such use as they require less manipulation to gain access to the target vessel and do not scrape the arterial wall. During use the curved region of the preformed shape of the device is dragged along and flipped within the vasculature as it goes in straight over a wire thereby providing more control to result in increased patient safety.

Figure 10A:
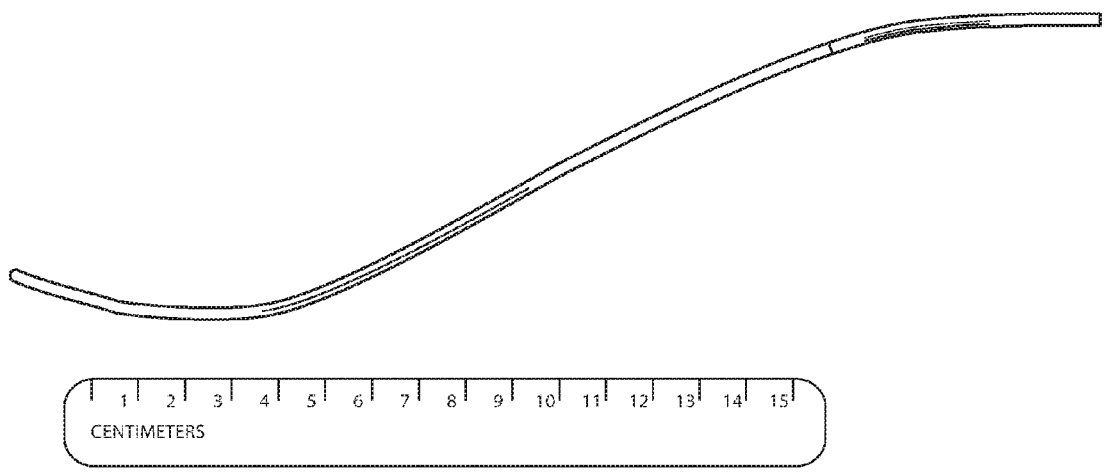
FIGS. 10A and 10B illustrate preformed shapes of embodiments of the steerable sheaths suitable for carotid access.
Figure 10B:
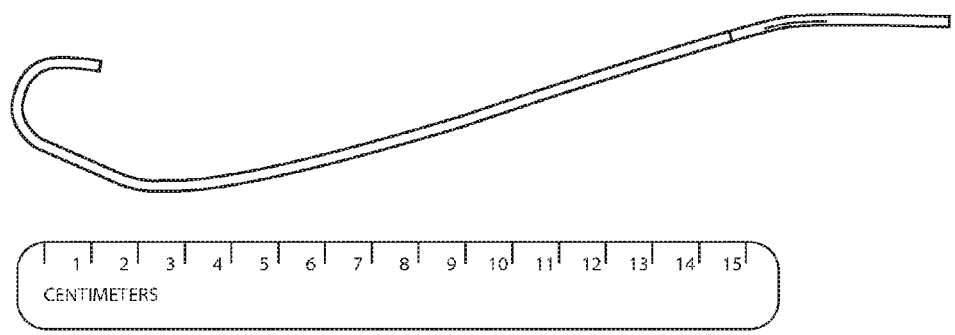

In a second embodiment suitable for carotid access, the sheath has a preformed curve in a shape substantially similar to that of the H1 catheter and the distal deflection portion of the device has a length of about 3 cm to about 5 cm and deflects around a tight radius of curvature of about 1 cm towards the proximal end of the catheter continuing the H1 curve direction and within the plane defined by the H1 curve (See FIGS. 10A and 10B).

On the right side of the heart, a steerable guide or introducer system provides a means to control the key procedures performed in these chambers of the heart, namely implantation of cardiac pacing leads, gaining access to the coronary sinus, and performing right heart biopsies for assessing cardiac transplant rejection. Here a steerable guide system has value for optimizing position of cardiac bioptomes which may be recorded in biplanar screen overlays or using an MRI Fusion System such as has been developed for cell therapy such that each biopsy site is recorded and not repeated. This enables the biopsies (performed four times per procedure with up to 20 procedures in the first year post heart transplant) to not hit the same spot twice and to avoid scar tissue which eliminates the value of the biopsies. Such a steerable biopsy system with a means to record locations also has value for biopsies used to obtain tissues for obtaining tissue to culture ex vivo for subsequent cardiac repair and regeneration strategies.

As described above, the steerable introducer sheath system comprises an introducer sheath having a proximal end and a distal end and a lumen extending from the proximal and to the distal end which can accommodate another catheter or device. The introducer sheath has a distal deflection portion that extends to said distal end and a main body portion that extends from the deflection portion to a handle on the proximal end. A coil is disposed within the wall of the introducer sheath and a braid is disposed coaxially about the coil. The braid is also disposed within the wall of the introducer sheath. The sheath has an average wall thickness of about 0.30 mm to about 0.50 mm. To deflect the deflection portion, a pull wire extends between the proximal end and the distal end of the introducer sheath. One end of the pull wires is secured to said distal deflection portion to control deflection of the distal deflection portion of said introducer sheath. A dilator is slidably disposed within the introducer sheath. At the proximal end of the introducer sheath, a hemostatic valve is fixed to the introducer sheath.

Any feature described in any one embodiment described herein can be combined with any other feature or features of any of the other embodiments whether preferred or not.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A steerable introducer sheath system adapted for delivery into a patient's vasculature, said steerable sheath system comprising:

an introducer sheath having a proximal end and a distal end and a lumen extending therethrough, said introducer sheath having a distal deflection portion that extends to said distal end and a main body portion that extends from said deflection portion to said proximal end, wherein said introducer sheath comprises a wall having a coil embedded within the wall of the introducer sheath and a braid disposed coaxially about the coil and embedded within the wall of the introducer sheath; and a pull wire extending between said proximal end and said distal end of said introducer sheath and having first and second ends, said first end being secured to said distal deflection portion to control deflection of the distal deflection portion of said introducer sheath;

a dilator slidably disposed within the introducer sheath;

a hemostatic valve fixed to the proximal end of the introducer sheath; wherein the deflection portion is characterized by a distal and a proximal end, and the braid terminates distally at a point proximate the proximal end of the deflection portion.

2. The device of claim 1, further comprising a handle with a lever arm coupled to said proximal end of said introducer sheath, said handle having a torsion spring mounted therein and having two ends, one end of said lever arm being secured to said torsion spring, and the other end of said lever arm being attached to said pull wire.

3. The device of claim 1, further including a pull wire tube extending along main body portion, said pull wire tube forming a lumen in which said pull wire is disposed.

4. The device of claim 1 further comprising a stiff portion disposed within the introducer sheath, extending circumferentially over an angle of about 5 to about 120 degrees and extending along said distal deflection portion, said introducer sheath comprising polymeric material, and said stiff portion comprising a material that has a durometer that is greater than the durometer of the polymeric material of the distal deflection portion of the introducer sheath.

5. The device of claim 4 wherein said stiff portion comprises a material that has an elastic modulus that is greater than the elastic modulus of the polymeric material of the distal deflection portion of the introducer sheath.

6. The device of claim 4, wherein said main body portion comprises a polymer having a durometer that is less than the durometer of said stiff portion.

7. The device of claim 4, wherein the durometer of said stiff portion ranges from and including 50 D to and including 90 D and the durometer of the polymeric material of the distal deflection portion of the introducer sheath ranges from 25 D to 60 D and the durometer of said stiff portion is greater than the durometer of said polymeric material of the distal deflection portion of the introducer sheath.

8. The device of claim 5, further including another stiff portion extending along said distal deflection portion.

9. The device of claim 5, wherein said coil comprises a plurality of turns and a connector connecting adjacent turns, where said connector forms a portion of said stiff portion.

10. The device of claim 5, wherein said introducer sheath has a longitudinal axis and said stiff portion extends parallel to the longitudinal axis of said introducer sheath.

11. The device of claim 5 or 7, wherein said introducer sheath has a circumference, said pull wire has a longitudinal axis and said stiff portion has a longitudinal axis and said axes are circumferentially spaced about 180 degrees from one another along the circumference of the introducer sheath.

12. The device of claim 5, wherein said stiff portion has a transverse cross-section that extends circumferentially about the distal deflection portion, said transverse cross-section defining an arc subtending an angle of about 10 degrees to about 70 degrees.

13. The device of claim 5, wherein said stiff portion comprises polymeric material.

14. The device of claim 5, wherein said stiff portion comprises metal.

15. The device of claim 5, wherein said stiff portion comprises nitinol.

16. The device of claim 1, wherein the coil disposed within the wall of the introducer sheath extends substantially the entire length of the deflection portion and main body portion.

17. The device of claim 16, wherein the distal deflection portion is characterized by a distal end and a proximal end, and wherein the braid terminates distally at the proximal end of the deflection portion and extends substantially the entire length of the main body portion.

18. The device of claim 1 wherein:
the wall has an average thickness of about 0.30 mm to about 0.50 mm; and
the introducer sheath has an inner diameter in the range of 4.5 F to 8.5 F.

* * * * *